United States Patent [19]

Linden

[11] Patent Number: 5,290,291
[45] Date of Patent: Mar. 1, 1994

[54] METHOD FOR IMPLANT REMOVAL

[75] Inventor: Harry A. Linden, Santa Barbara, Calif.

[73] Assignee: Hall Surgical, Division of Zimmer, Inc., Santa Barbara, Calif.

[21] Appl. No.: 851,597

[22] Filed: Mar. 16, 1992

[51] Int. Cl.⁵ ............................................... A61F 5/04
[52] U.S. Cl. ................................... 606/99; 606/86
[58] Field of Search .................. 606/86, 90, 94, 99, 606/104, 107; 433/86

[56] References Cited

U.S. PATENT DOCUMENTS

| | | | |
|---|---|---|---|
| 4,248,232 | 2/1981 | Engelbrecht et al. | 128/305 |
| 4,399,813 | 8/1983 | Barber | 128/92 EC |
| 4,476,861 | 10/1984 | Dimakos et al. | 128/303 R |
| 4,612,922 | 9/1986 | Barber | 128/92 EB |
| 4,702,236 | 10/1987 | Tarabichy et al. | 128/92 V |
| 4,846,161 | 7/1989 | Roger | 128/92 V |
| 4,873,969 | 10/1989 | Huebsch | 128/92 R |
| 4,919,153 | 4/1990 | Chin | 606/93 |
| 4,986,826 | 1/1991 | Roger | 606/82 |
| 5,019,083 | 5/1991 | Klapper et al. | 606/99 |
| 5,027,792 | 7/1991 | Meyer | 128/6 |
| 5,041,120 | 8/1991 | McColl et al. | 606/99 |
| 5,045,054 | 9/1991 | Hood et al. | 604/22 |
| 5,055,043 | 10/1991 | Weiss et al. | 433/86 |
| 5,064,426 | 11/1991 | Huebsch | 606/92 |

FOREIGN PATENT DOCUMENTS 9107138 5/1991 PCT Int'l Appl. .

Primary Examiner—David Isabella
Assistant Examiner—Debra S. Brittingham
Attorney, Agent, or Firm—Cary R. Reeves

[57] ABSTRACT

An implant being securely fixed in a bone by a layer of plastic cement is removed by supplying a pressurized fluid to the interface between the cement and the implant.

2 Claims, 2 Drawing Sheets

METHOD FOR IMPLANT REMOVAL

BACKGROUND OF THE INVENTION

The present invention relates to a method and an apparatus for facilitating the removal of a prosthetic implant from a body and, more specifically, to the use of fluid pressure to effect said removal.

An orthopaedic implant is typically placed in a bone having a prepared bed formed to the implant shape. The bed fits the implant loosely and a plastic cement fills the space between the implant and the bone to securely fix the implant. Due to implant failure or other complications it is occasionally necessary to remove the implant. A variety of means have been proposed for such removal including impacting devices for driving the implant out, powered and manual instruments for excavating the cement from about the implant, and means for heating or ultrasonically vibrating the implant or instruments to soften the cement. These prior devices have been employed with varying levels of safety, efficacy, and economy. Further, they have been limited to use with rigid metallic implants because of their dependence on energy being conducted through the implant.

SUMMARY OF THE INVENTION

The invention of this disclosure provides a reliable, uncomplicated method and means to safely remove an orthopaedic implant by employing fluid pressure applied directly to the interface between the implant and the cement to deform the cement and thereby loosen the implant. The invention may be effectively employed with implants constructed of a variety of materials, even those that are highly flexible or that are insulators with respect to thermal and vibratory energy. Such materials include plastics, composites and ceramics, which constitute an increasingly important group of implant materials.

DETAILED DESCRIPTION OF THE INVENTION

Figure 1:
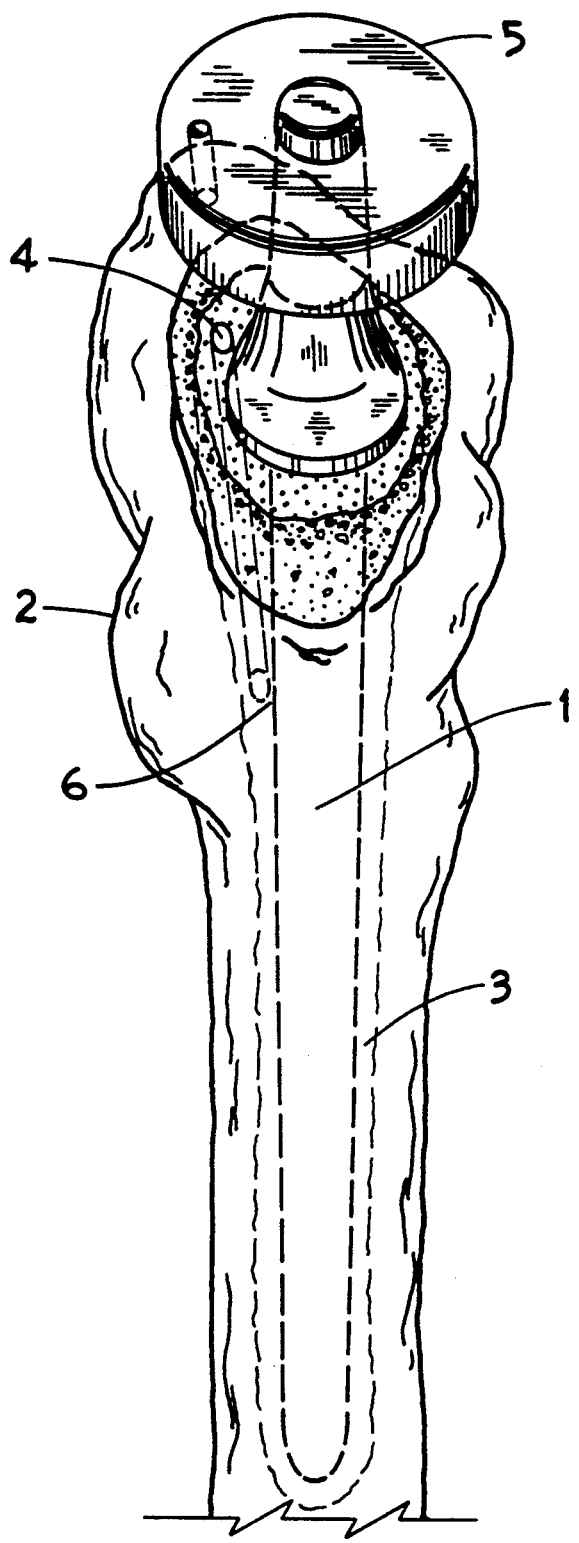
FIG. 1 is a perspective view of an implant in situ.
Figure 2:
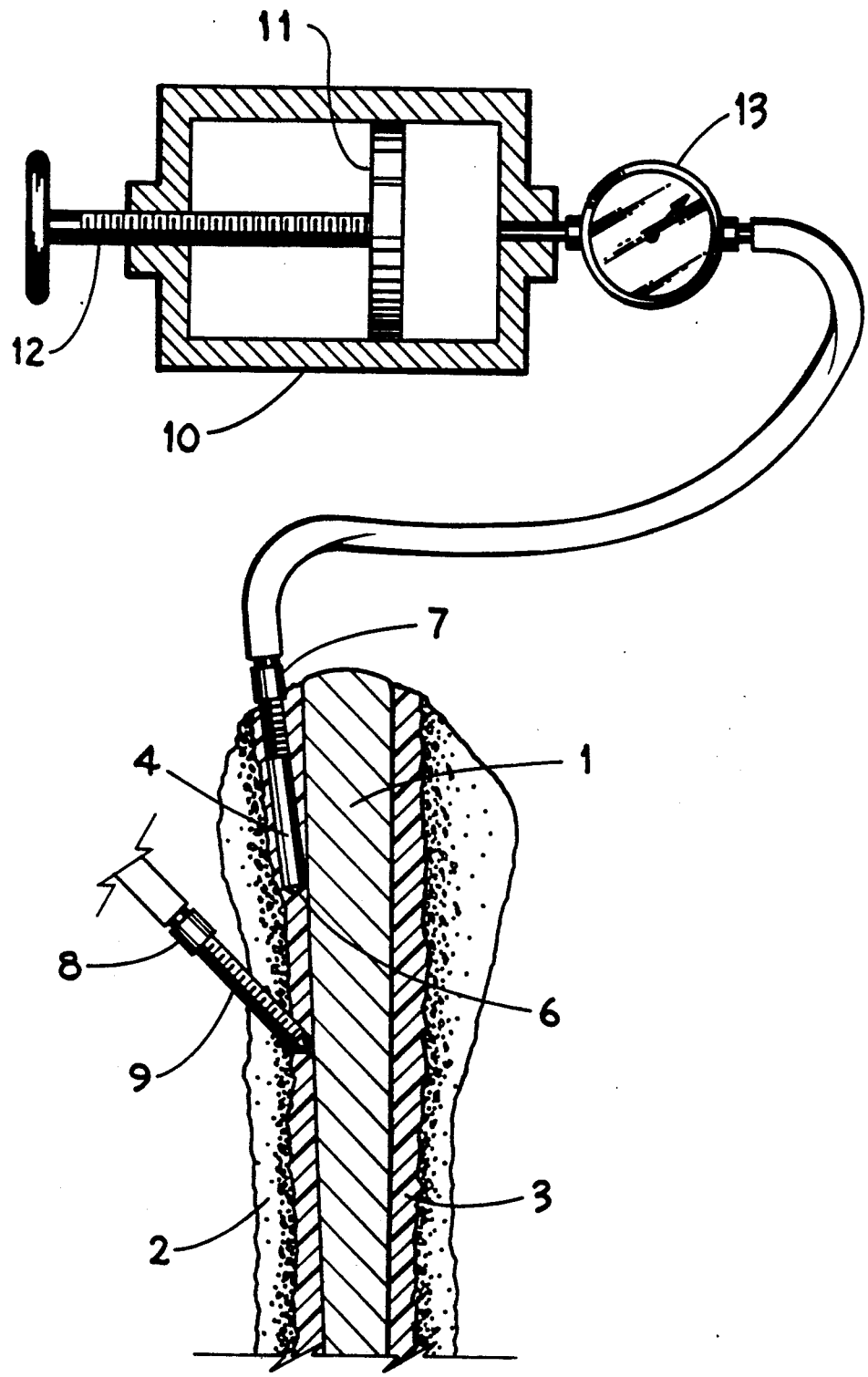
FIG. 2 is a partial sectional view of the apparatus of the invention showing its interaction with a portion of an implant and bone.

Referring to FIGS. 1 and 2, an exemplary implant 1 is depicted as a femoral hip implant cemented into a human femur 2. The implant is secured in the femur by a layer 3 of acrylic bone cement which grips the implant due to interdigitation with micro and macro surface features along the interface, or bond line, which exists between the cement and implant. The implant may be loosened according to the present invention by pressurizing fluid at the interface. The fluid pressure stretches the cement enough to relieve its grip on the implant. The cement layer is also vulnerable to fracture and separation due to the fluid pressure. Such separation would likely occur at regions of minimum cross sectional thickness. This method and apparatus can be applied to any suitable implant including femoral and acetabular hip implants, femoral and tibial knee implants, shoulder implants, and elbow implants. It may also be employed with any fixing material including plastic bone cements, plasters, and other luting agents.

Fluid access to the interface may be provided by creating an access port 4 through the cement layer, such as by drilling. Drilling may be aided by a drill guide 5, as shown in FIG. 1, which attaches to the implant and directs the drill to an appropriate region 6 of the interface. Likewise, a port could be made in the implant. Fluid access may also be provided by holes or channels already existing in the cement or implant. Such an access port could be part of the implant when it is sold. Fluid is then supplied to the interface. Any fluid may be used, however, the fluid is preferably an incompressible liquid such as saline. It is also preferable that the fluid is introduced so as to eliminate air from the port. This can be accomplished by injecting fluid into the port from the bottom using a hypodermic needle. Next the port is sealed with a pressure fitting 7. Any fitting that will form a seal with the port may be used. Suitable fittings include a threaded fitting, a tapered press fitting, and a cemented fitting. An alternate fitting 8 may include a portion 9 to extend substantially to the bottom of the port to improve the seal or to extend through a portion of bone. The fitting should be well sealed to the port. During pressurization the fitting will be subject to a separation force. For example, a fixing material such as polymethly-methacrylate (PMMA) bone cement has a tensile strength of approximately 8000 psi. If a port 0.040 inches in diameter is used, then a separation force of ten pounds would be exerted on the fitting at 8000 psi. The fitting is connected to a pressurizing device such as a cylinder 10 having a piston 11 advanced by a screw 12. Preferably the system includes a pressure gauge 13 for monitoring the fluid pressure.

A system as described above and that is well sealed to prevent leaks is inherently safe as explained in the following description of its operation. The screw is turned to advance the piston which forces fluid into the port and thereby increases the fluid pressure at the interface. When the pressure reaches a critical value the cement will separate from the implant or the cement will fracture or both. As this occurs, the fluid pressure will decrease dramatically so that a high pressure fluid can not be injected into the bone. Furthermore, only a small volume of fluid is necessary. The piston can be advanced again. If the crack or separation is only partial, the pressure will build rapidly again and the cycle will repeat. If the crack or separation is complete then the pressure will not build and the implant can be removed or pressure can be applied to another region of the interface.

While a piston advanced by a screw has been described, any means for pressurizing the fluid may be used including various manual and powered pumps or pneumatically charged chambers. In the case of a device that can continue to supply pressure it is desirable to include means to monitor the pressure and suspend the supply when a crack or separation is detected. Mechanical energy in addition to the fluid pressure may be advantageously applied to the implant. Striking, pulling, or vibrating the implant prior to, in conjunction with, or after supplying fluid pressure to the implant may aid in loosening the implant according to this method.

While the foregoing has described an exemplary preferred embodiment of the present invention, it will be understood by those skilled in the art that modifications can be made without departing from the spirit and scope of the invention defined by the appended claims.

I claim:

1. A method for separating an implant secured to a bone with a fixing material from the fixing material, said fixing material forming an interface between the bone and said implant, comprising the steps of:
    utilizing a fluid;
    supplying the fluid to the interface;
    providing means cooperating with the interface for increasing pressure of the fluid at the interface; and
    increasing the pressure in the fluid at the interface.

2. A method for separating an orthopedic implant from a surrounding layer of cement, the cement forming an interface with the implant, comprising the steps of:
    drilling a port through the cement to a point adjacent the interface;
    connecting the port to a pump via means for providing substantially leak free fluid access to the interface;
    activating the pump to supply a fluid to the interface;
    continuing to activate the pump in order to increase pressure in the fluid at the interface; and
    removing the implant from the cement.

* * * * *